(12) United States Patent
Kaplan et al.

(10) Patent No.: US 9,144,635 B1
(45) Date of Patent: Sep. 29, 2015

(54) EASILY DISINFECTED BULB-SYRINGE

(71) Applicants: Glen Kaplan, Palm Coast, FL (US); Candice Koehler, Palm Coast, FL (US)

(72) Inventors: Glen Kaplan, Palm Coast, FL (US); Candice Koehler, Palm Coast, FL (US)

(73) Assignee: IBIZ INNOVATIONS, LLC, Palm Coast, FL (US)

( * ) Notice: Subject to any disclaimer, the term of this patent is extended or adjusted under 35 U.S.C. 154(b) by 0 days.

(21) Appl. No.: 14/320,410

(22) Filed: Jun. 30, 2014

Related U.S. Application Data

(60) Provisional application No. 61/841,809, filed on Jul. 1, 2013.

(51) Int. Cl.
| | | |
|---|---|---|
| *A61M 31/00* | (2006.01) | |
| *A61M 5/00* | (2006.01) | |
| *A61M 1/00* | (2006.01) | |

(52) U.S. Cl.
CPC ......... *A61M 1/0009* (2013.01); *A61M 2205/19* (2013.01); *A61M 2210/0618* (2013.01)

(58) Field of Classification Search
CPC .............................. A61M 31/00; A61M 5/00
See application file for complete search history.

(56) References Cited

U.S. PATENT DOCUMENTS

| | | | |
|---|---|---|---|
| 901,100 A | 10/1908 | Heitman | |
| 1,971,345 A | 8/1934 | Hein | |
| 2,815,754 A | 12/1957 | Hoffman et al. | |
| 3,215,142 A | 11/1965 | Buono | |
| 3,354,883 A | 11/1967 | Southerland | |
| 3,705,583 A | 12/1972 | Rentsch | |
| 3,705,584 A | 12/1972 | Fript | |
| 4,223,810 A * | 9/1980 | Sneider | 222/107 |
| 4,240,422 A | 12/1980 | Hazen | |
| 4,258,714 A | 3/1981 | Leopoldi et al. | |
| 4,693,709 A | 9/1987 | George et al. | |
| 5,817,066 A | 10/1998 | Goforth | |
| 5,848,993 A * | 12/1998 | Tanhehco et al. | 604/217 |
| 6,120,478 A | 9/2000 | Moore et al. | |
| 7,918,882 B2 * | 4/2011 | Pavcnik et al. | 623/1.13 |

(Continued)

FOREIGN PATENT DOCUMENTS

WO    2007146921 A2    12/2007

OTHER PUBLICATIONS

Park, J. "Biomaterials: An Introduction". Springer Science and Business Media: Jul. 23, 2007. pp. 183.*

(Continued)

*Primary Examiner* — Tatyana Zalukaeva
*Assistant Examiner* — Sara Sass
(74) *Attorney, Agent, or Firm* — Brian S. Steinberger; Law Offices of Brian S. Steinberger, P.A.

(57) ABSTRACT

A bulb syringe has a hollow spheroidal bulb which is split into two separate hemispheroidal portions transaxially defining an upper portion and a lower portion. The separate hemispheroidal portions are joined at a transaxial juncture of the upper and lower portions, and are able to be separated for disinfecting and later rejoined. One of the upper and lower portions extends into an elongated tubular spout terminating at an opening which is in communication with an interior volume of the spheroidal bulb. The tip of the spout is able to be positioned within the nostrils of an infant or small child. The two portions may be joined by molded-in mechanical threads or by an external circumferential strip with barbs that penetrate overlapping walls of the bulb at the joint between upper and lower portions but does not fully puncture the bulb.

2 Claims, 5 Drawing Sheets

(56) References Cited

U.S. PATENT DOCUMENTS 8,348,906 B2    1/2013    Tanaka et al.
8,696,648 B2    4/2014    Laerdal et al.
D712,535 S      9/2014    Du

OTHER PUBLICATIONS

BoogieBulb, The First True Cleanable & Reusable Baby Nasal Aspirator Syringe, The Baby Nasal Aspirator that Saves you $100's, http://boogiebulb.com/, Mar. 6, 2015, 14 pages.

\* cited by examiner

EASILY DISINFECTED BULB-SYRINGE

BACKGROUND

This disclosure relates to irrigation and aspiration devices such as syringes.

Irrigation and aspiration of fluids at the nose, ear, anus, and vagina are common procedures practiced by medical staff and by the general public at large. Nasal congestion in particular of babies is often relieved through the use of a common bulb syringe. Nasal congestion in an infant in the first few months of life can interfere with breastfeeding and cause respiratory distress. Nasal congestion can interfere with a child's ears, hearing, and speech development. Significant congestion may interfere with sleep, cause snoring, and may be associated with sleep apnea.

In order to treat nasal congestion in an infant, various devices for irrigating and aspirating mucus from the nose have been developed. A nasal syringe, also known as a nasal bulb, or bulb syringe is a simple yet effective device for removing mucus. However, such a syringe may become contaminated as it is not easily cleaned out and sterilization may not be impossible, while verification of the bulb syringe's interior cleanliness is virtually impossible.

The present disclosure solves these problems by providing a bulb syringe that is able to be opened for visual inspection and for manual scrubbing to disinfect it.

BRIEF DESCRIPTION OF THE SEVERAL VIEWS OF THE DRAWINGS

Like reference numerals in the various figures indicate like elements.

DETAILED DESCRIPTION

Figure 1:
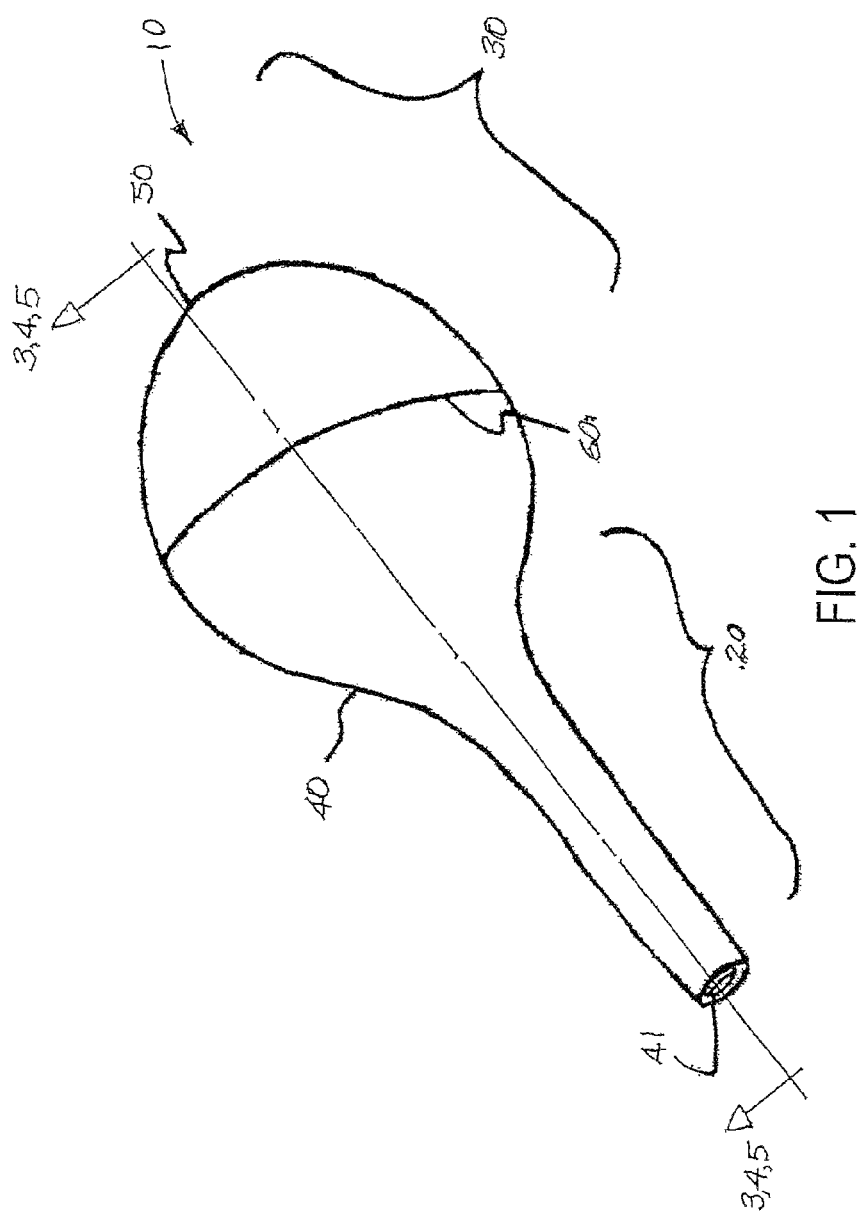
FIG. 1 is an example perspective view of a bulb syringe as disclosed herein.

The present disclosure, as shown in FIG. 1, is a bulb syringe 10 capable of aspiration and irrigation functions and comprises a hollow spheroidal bulb 30 which is split into two separate hemispheroidal portions transaxially, an upper portion 50 and a lower portion 40 wherein the portions 40 and 50 may be tightly joined at a circumferential (transaxial) juncture 60 which may be secured using several different means as will be described. The lower portion 40 has an elongated tubular spout 20 extending axially and terminating at an opening 41 which is in communication with an interior volume 70 (FIG. 2) within syringe 10.

Figure 2:
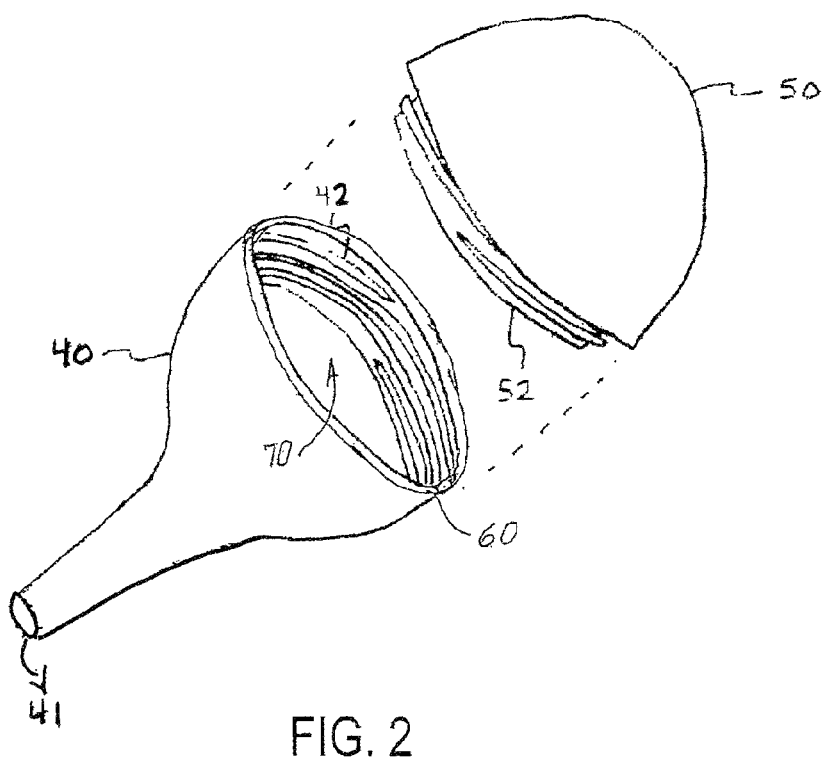
FIG. 2 is an exploded perspective view thereof in an embodiment.
Figure 3:
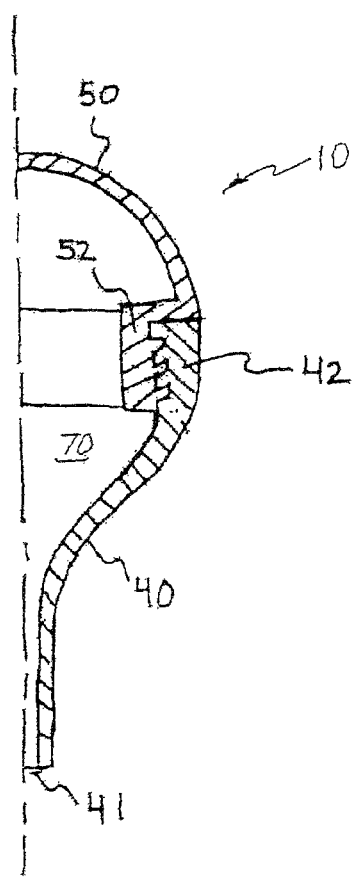
FIG. 3 is a half section view thereof taken along cutting line 3-3 in FIG. 1, the missing other half section view is a mirror image of the section shown.

In FIG. 2 we see that juncture 60 may be threaded. In this embodiment, matching threads 42 and 52 on adjoining portions 40 and 50 respectively may be mutually engaged to bring portions 40 and 50 tightly together as shown in FIG. 3. Bulb 30 is molded with a relatively thin wall of a rubber material or rubber and elastomer material mix in order to obtain a maximum suction volume (interior volume 70), which enables a maximum expulsion of gas or liquid. However, in order to achieve strong and deep threads, the threaded portions of bulb portions 40 and 50 must be formed thicker and this tends to limit bulb flexibility as well as interior volume 70. The advantage of being able to separate portion 50 from portion 40 is, of course, that it provides for visual inspection of the interior surfaces and enables manual scouring to achieve the maximum cleanliness of interior volume 70. When syringe 10 is used to clean the nose of a child, mucus may remain within bulb 30 even after rinsing syringe 10 with hot water. Bacteria may grow within bulb 30 and contaminate the child when next used. The only certain way to know if bulb 30 is fully cleansed is by visual inspection.

Figure 4:
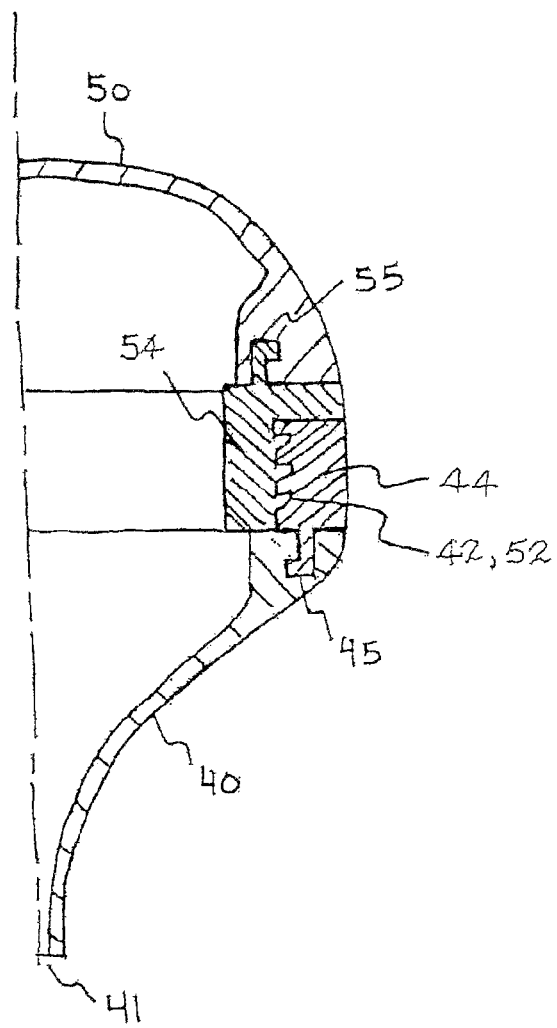
FIG. 4 is further half section view as in FIG. 3 of a further embodiment, the missing other half section view is a mirror image of the section shown.

The threaded joint shown in FIGS. 2 and 3 may not be fully secure in that the soft material of which bulb 30 is made may be too soft to enable a fully tight joint or may separate when bulb 30 is squeezed. FIG. 4 shows a further embodiment wherein inserts 44 and 54 provide threads 42, 52. Inserts 44, 54 may be made of a stiffer plastic material than the material of bulb 30 and this stiffer material may be able to secure a very tight joint. Inserts 44 and 54 may be permanently engaged with bulb portions 40 and 50 respectively as shown and may be molded in place using engagement fingers 45 and 55. Engagement finger 45 can have an L shape with a square shaped free end extending in a first direction. Engagement finger 55 can have an L shape with a square shaped free end extending in a second direction opposite to the first direction. This embodiment may guarantee a secure joint but also reduces the flexibility and volume of bulb 30.

Figure 5:
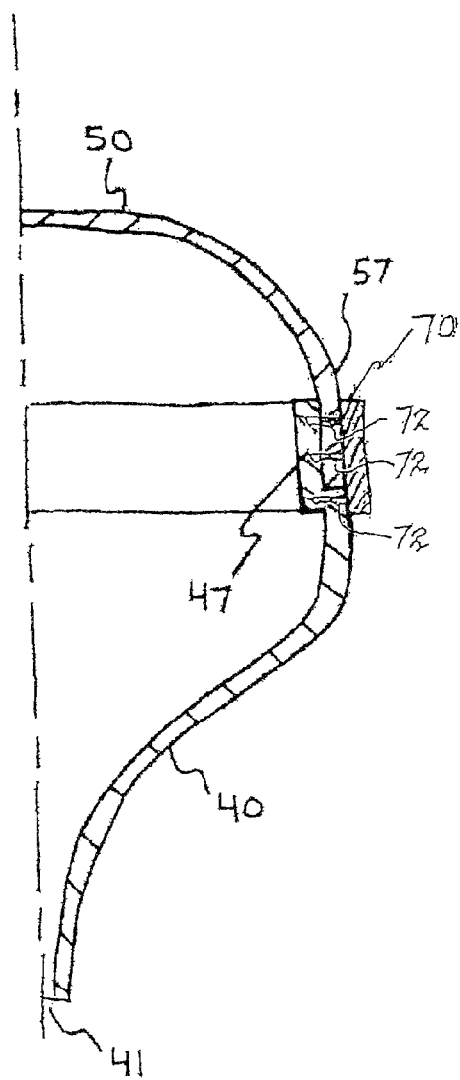
FIG. 5 is a further half section view as in FIG. 3 of a still further embodiment, the missing other half section view is a mirror image of the section shown.

A still further embodiment is shown in FIG. 5. In this approach, the walls of bulb 30 are thin and highly flexible as required. The wall portions 47 and 57 are molded to overlap as shown, and a strip 70 is wrapped circumferentially around the joint on the exterior of bulb 30. Strip 70 has barbs 72 which may be pressed into wall portions 47 and 57 as shown penetrating both layers. When bulb 30 is squeezed strip 70 moves inwardly with wall portions 47 and 57 maintaining the secure joint. Strip 70 may be a highly flexible material such as a fabric and may be removed and replaced multiple times for interior inspection of bulb 30. This embodiment has the advantages of being highly flexible, maintaining relatively thin walls of portions 40 and 50, and providing maximum interior volume 70.

Lower portion 40 and upper portion 50 may be formed of the same material, for example a soft, flexible, or pliable rubber. Alternatively, lower portion 40 may be formed of a hard or rigid plastic and upper portion 50 may be formed of a softer rubber and this may provide a stiffer and more durable joint, but has the disadvantage of providing less expressed volume per squeeze. In any configuration, bulb 30, or at least upper portion 50 is flexible enough to permit manual compression thereby forcing air or other fluid out of bulb 30 through spout 20. Air or other fluid may then be aspirated into syringe 10 by releasing the compressive force from bulb 30 whereby the natural elastic restoring force of bulb 30 causes it to resume its spheroidal shape providing a strong suction.

A general method of use of bulb 30 includes holding syringe 10 in one hand and squeezing the sides and/or top of bulb 30. Opening 41 is then placed adjacent to or slightly inside of a person's or child's nostril. Pressure upon bulb 30 is then released, allowing mucus to be aspirated into syringe 10. Syringe 10 is removed from the nose and the aspirated mucus squeezed out into a waste receptacle. Syringe 10 may be opened as described to inspect its interior surfaces and to clean it.

Embodiments of the subject apparatus and method have been described herein. Nevertheless, it will be understood that various modifications may be made without departing from the spirit and understanding of this disclosure. Accordingly, other embodiments and approaches are within the scope of what has herein been described and embodied in the appended claims.

What is claimed is:

1. A bulb syringe comprising:
a hollow spheroidal bulb split into two separate hemispheroidal portions transaxially defining an upper portion and a lower portion of the spheroidal bulb wherein the separate hemispheroidal portions are joined at a transaxial juncture of the upper portion and a lower portion, wherein the upper portion and a lower portion are enabled to be separated and rejoined, the transaxial portion having a threaded interconnect joining the upper and lower portions;
an upper threaded insert secured to the upper portion by an upper engagement finger extending into the upper portion, the upper threaded insert made of a stiffer material than walls of the bulb syringe, the upper engagement finger having an L shape with a square shaped free end extending in a first direction;
a lower threaded insert secured to the lower portion by a lower engagement finger extending into the lower portion, the lower threaded insert made of stiffer material than walls of the bulb syringe, the lower engagement finger having an L shape with a square shaped free end extending in second direction opposite to the first direction; and
the lower portion having an elongated tubular spout extending axially and terminating at an opening, said opening in communication with an interior volume within the bulb.

2. A bulb syringe comprising: a hollow spheroidal bulb split into two separate hemispheroidal portions transaxially defining an upper portion and a lower portion of the spheroidal bulb wherein the separate hemispheroidal portions are joined at a transaxial juncture of the upper portion and a lower portion, the transaxial juncture having a horizontal longitudinal axis, wherein the upper portion and a lower portion are enabled to be separated and rejoined; the lower portion having an elongated tubular spout extending axially and terminating at an opening, said opening in communication with an interior volume within the bulb; an upper vertical edge extending downward from the upper portion; the vertical edge of the upper portion having a longitudinal axis substantially perpendicular to the horizontal axis along the transaxial juncture; a lower vertical edge extending upward from the lower portion, the vertical edge of the lower portion having a longitudinal axis axes substantially perpendicular to the horizontal axis along the transaxial juncture, the upper vertical edge and the lower vertical edge mutually overlap to be side by side one another; the two separate hemispheroidal portions attach at a joint, where this attachment consists of a flexible strip and barbs, the flexible strip positioned to wrap around the overlap of the upper vertical edge and the lower vertical edge along the transaxial juncture of the bulb syringe; and the barbs extending inward from the flexible strip, the barbs having longitudinal axes oriented perpendicular to the longitudinal axes of the upper vertical edge and the lower vertical edge, so that the side by side vertical edges at the transaxial axis of the upper and lower portions are impaled together by the barbs securing the upper and lower portions at the transaxial juncture, where the barbs include upper barbs and lower barbs parallel to one another, and the strip is comprised of a fabric material different from the spheroidal bulb.

* * * * *